United States Patent [19]

Orban et al.

[11] Patent Number: 4,492,791

[45] Date of Patent: Jan. 8, 1985

[54] PROCESS FOR THE PREPARATION OF POLYAMINOTRIAZINES

[75] Inventors: Ivan Orban; Eduard Troxler, both of Basel, Switzerland

[73] Assignee: Ciba Geigy Corporation, Ardsley, N.Y.

[21] Appl. No.: 488,246

[22] Filed: Apr. 25, 1983

[30] Foreign Application Priority Data

May 4, 1982 [CH] Switzerland ............... 2732/82

[51] Int. Cl.³ .......................................... C07D 401/14
[52] U.S. Cl. ................................. 544/198; 544/209
[58] Field of Search .............................. 544/198, 209

[56] References Cited

U.S. PATENT DOCUMENTS

| 4,086,204 | 4/1978 | Cassandrini et al. | 260/45.8 NT |
| 4,335,242 | 3/1982 | Wiezer et al. | 544/198 |
| 4,400,505 | 8/1983 | Loffelman et al. | 544/209 |
| 4,409,348 | 10/1983 | Wiezer et al. | 544/209 |

*Primary Examiner*—John M. Ford
*Attorney, Agent, or Firm*—Luther A. R. Hall

[57] ABSTRACT

The known reaction of dichlorotriazines of the formula II

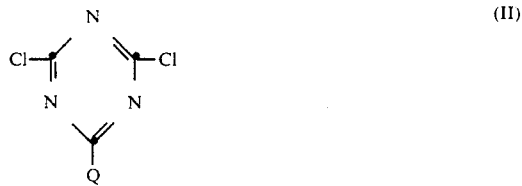

in which Q is an ether or amino radical, with diamines of the formula III Pip—NH—R—NH—Pip     (III)

in which Pip is a radical of the formula

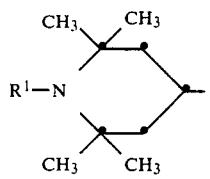

in which $R^1$ is hydrogen, $C_1$-$C_{12}$-alkyl, $C_3$-$C_8$-alkenyl, $C_7$-$C_{11}$-phenylalkyl, $C_2$-$C_8$-alkanoyl or $C_3$-$C_5$-alkenoyl and R is a divalent organic radical leads to undesirable, sparingly soluble by-products. The formation of these by-products can be suppressed if the reaction is carried out in a water-immiscible organic solvent with the addition of an aqueous base—preferably NaOH or KOH—under pressure at 140°–220° C.

8 Claims, No Drawings

PROCESS FOR THE PREPARATION OF POLYAMINOTRIAZINES

The invention relates to an improved process for the preparation of polyaminotriazines by polycondensation of dichlorotriazines with secondary diamines which are substituted on the nitrogen by 2,2,6,6-tetramethylpiperidin-4-yl radicals.

German Offenlegungsschrift No. 2,636,144 discloses compounds of the formula

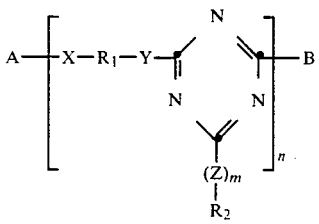

in which X, Y and Z are —O—, —NH— or —NR$_3$—, R$_1$ is a divalent organic radical, R$_2$ and R$_3$ are monovalent radicals and at least one of the radicals R$_2$ or R$_3$ is a polyalkylpiperidine radical, m is zero or 1, n is a number from 2 to 200 and A and B are end groups. Such compounds are excellent light stabilisers, especially for organic polymers, and are used industrially for stabilising plastics. According to German Offenlegungsschrift No. 2,636,144, these polyaminotriazines are prepared by polycondensation of a dichlorotriazine of the formula

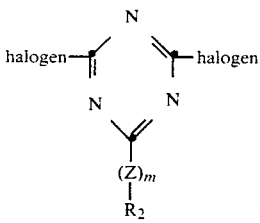

or of a cyanuric halide in an inert solvent at a temperature of −10° up to the boiling point of the solvent, in the presence of an organic or inorganic base.

In the examples, the reaction is chiefly carried out in boiling toluene, and anhydrous NaOH is used as the base. The mixture is worked up by filtering off the NaCl formed and evaporating off the solvent. This process has the disadvantages that the reaction does not proceed to completion, and that sparingly soluble by-products, in particular cyclic by-products, are formed. Because these products are sparingly soluble, they are undesirable as stabilisers and must be separated off from the linear polycondensate by filtration. Besides the loss in yield resulting from the formation of these by-products, there is the disadvantage that the by-products are very difficult to filter off since they are in a very finely pulverulent form and thereby block the filter pores. After these undesirable by-products have been separated off, the yield in the process given is thus only about 70–75%. A third disadvantage of the process is that only products having a relatively low degree of polycondensation n<6 can be obtained. A low n is generally desirable if the products are used as stabilisers, but products having a higher molecular weight would be desirable for particular purposes.

If an excess of NaOH is used to improve the yield of the known process, an increased amount of insoluble by-products are formed, and partial hydrolysis of the halogen on the triazine ring occurs, so that no substantial increase in the yield of linear polyaminotriazines is achieved.

German Offenlegungsschrift No. 2,933,078 discloses quite similar polyaminotriazines which are likewise prepared by polycondensation in boiling toluene or xylene, with addition of anhydrous NaOH. In this case also, only products of very low molecular weight are obtained, and the yield is inadequate.

It has now been found that the disadvantages described can largely be avoided if the reaction is carried out at elevated temperatures in a two-phase system. For this, a water-immiscible solvent in which the starting materials and end products are soluble and, as the base, a concentrated aqueous solution of an inorganic base are used. The reaction is carried out under pressure, so that elevated temperatures can be applied.

The invention thus relates to a process for the preparation of compounds of the formula I

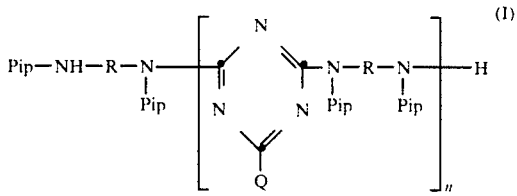

in which n is a number from 2 to 20, Pip is a radical of the formula

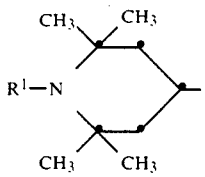

in which R$^1$ is hydrogen, C$_1$–C$_{12}$-alkyl, C$_3$–C$_8$-alkenyl, C$_7$–C$_{11}$-phenylalkyl, C$_2$–C$_8$-alkanoyl or C$_3$–C$_5$-alkenoyl, R is C$_2$–C$_{12}$-alkylene, which can be interrupted by —O— or —NR$^2$—, in which R$^2$ is hydrogen, C$_1$–C$_{12}$-alkyl, C$_3$–C$_{13}$-alkoxyalkyl, cycloalkyl or Pip, or R is a divalent cycloaliphatic C$_6$–C$_{15}$-radical, and Q is a radical of the formula —OR$^3$, —NHR$^4$ or —NR$^4$R$^5$, in which R$^3$ is C$_1$–C$_{12}$-alkyl, C$_3$–C$_{12}$-alkoxyalkyl, cyclohexyl, benzyl, phenyl, tolyl or Pip, R$^4$ is C$_1$–C$_{12}$-alkyl, C$_3$–C$_{12}$-alkoxyalkyl, C$_4$–C$_{12}$-dialkylaminoalkyl, allyl, benzyl, cyclohexyl, phenyl, tolyl or Pip and R$^5$ is C$_1$–C$_{12}$-alkyl, C$_3$–C$_{12}$-alkoxyalkyl or cyclohexyl, or R$^4$ and R$^5$ together with the N atom to which they are bonded form a 5- or 6-membered heterocyclic ring, by polycondensation of 1 mol of a dichlorotriazine of the formula II

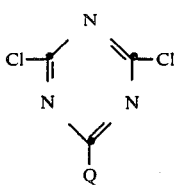

(II)

with 1.00 to 1.20 mols of a diamine of the formula III

Pip—NH—R—NH—Pip (III)

in an inert organic solvent with addition of a base, wherein an aqueous solution of an inorganic base is used as the base, a water-immiscible solvent is used, and the reaction is carried out at 140°–220° C. under pressure.

R can be a straight-chain or branched alkylene radical which may be interrupted by —O— or —NR²—. Examples of R are 1,2-ethylene, tri-, tetra-, penta-, hexa-, octa-, deca- or dodeca-methylene, 2,2,4- or 2,4,4-trimethylhexamethylene, 4-oxahept-1,7-ylene, 4,7-dioxadec-1,10-ylene, 4-(methylaza)-hept-1,7-ylene, 4-(cyclohexylaza)-hept-1,7-ylene and 4-(1,2,2,6,6-pentamethyl-4-piperidyl-aza)-hept-1,7-ylene. R can also be a cycloaliphatic radical, for example 1,3- or 1,4-cyclohexylene, dicyclohexylmethane-4,4'-diyl or a radical of the formula

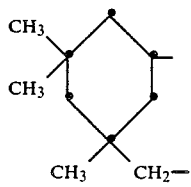

An alkyl radical $R^1$, $R^2$, $R^3$, $R^4$ or $R^5$ can be, for example, methyl, ethyl, propyl, isopropyl, n-butyl, tert.-butyl, isoamyl, n-hexyl, 2-ethylhexyl, n-octyl, ditert.-octyl, n-decyl or n-dodecyl.

An alkoxyalkyl radical $R^3$, $R^4$ or $R^5$ can be, for example, 2-methoxyethyl, 2-ethoxyethyl, 3-ethoxypropyl, 3-butoxypropyl or 3-isopropoxypropyl. A dialkylaminoalkyl radical $R^4$ can be, for example, 2-dimethylaminoethyl, 3-dimethylaminopropyl, 3-diethylaminopropyl or 3-dibutylaminopropyl.

An alkenyl radical $R^1$ can be, for example, allyl, methallyl or dimethylallyl. A phenylalkyl radical $R^1$ can be, for example, benzyl, phenethyl or phenylpropyl. An alkanoyl radical $R^1$ can be, for example, acetyl, propionyl, butyroyl, hexanoyl or octanoyl. An alkenoyl radical $R^1$ can be, for example, acryloyl, methacryloyl or crotonoyl.

This process permits virtually quantitative conversion and a high yield of linear polytriazines of the formula I. Not only is the conversion increased, but also the formation of the sparingly soluble by-products is suppressed, and these are obtained in a coarser form in which they can be filtered more easily. A serious industrial problem is thereby solved.

Moreover, on the basis of the high conversion, it is possible to obtain products with a high degree of polycondensation n. However, if products having a low n are required, these can also be obtained in the present process in a conventional manner by using an appropriate excess of the diamine III.

A small excess of diamine is advantageous. A 0–20 mol %, preferably a 2–5 mol %, excess of III is used, depending on the desired molecular weight or degree of polycondensation. Degrees of polycondensation n of 2–20, preferably 4–10, are thereby achieved.

It is surprising that, when an aqueous base is used, the formation of sparingly soluble by-products is suppressed and the yield is increased. According to the literature, it was to be expected that the Cl atoms would be saponified under aqueous/alkaline conditions in a temperature range above 140° C.

The process can be carried out with a large number of dichlorotriazines of the formula II and diamines of the formula III. However, those dichlorotriazines of the formula II in which Q is a radical —NHR and those diamines of the formula III in which R is a straight-chain or branched $C_4$–$C_{12}$-alkylene radical and $R^1$ is hydrogen or methyl are preferably used. Dichlorotriazines of the formula II in which Q is the radical —NH—$C_6$—$C_{12}$-alkyl and those diamines of the formula III in which R is hexamethylene and $R^1$ is hydrogen or methyl are particularly preferred.

The dichlorotriazines of the formula II can be prepared from cyanuric trichloride and a monofunctional compound QH, such as is described in German Offenlegungsschrift No. 2,636,144 or in German Offenlegungsschrift No. 2,933,078. The reaction solution thereby obtained can be used for the present process, without the compound II being isolated. However, the compound II is preferably isolated before it is further reacted.

The diamines of the formula III can be prepared by hydrogenating amination of triacetonamine, such as is described in German Offenlegungsschrift No. 2,611,208.

The organic solvents are, in particular, hydrocarbons, for example toluene, xylene, mesitylene, tetralin, decalin and higher alkylbenzenes, for example nonylbenzene and dodecylbenzene and mixtures of such alkylbenzenes.

The inorganic bases are, in particular, those which are highly soluble in water, for example alkali metal hydroxides and alkali metal carbonates. Sodium hydroxide or potassium hydroxide is preferably used, and the reaction is preferably carried out using 30–60%, in particular about 50%, solutions of the inorganic base.

The temperatures used are higher than those which have hitherto been described, and the reaction is preferably carried out at 170°–190° C. A closed vessel is used, so that increased pressure results from the vapour pressures of the solvent and of the water prevailing at the reaction temperature. This increased pressure is about 0.5–1 MPa, so that it is not necessary to carry out the reaction in a thick-walled autoclave. The reaction is preferably carried out in a pressure-resistant stirred kettle. Stirring should not be intensive, and turbulent mixing of the two phases is to be avoided. The use of an anchor-type stirrer at a speed of 40–45 rpm is to be recommended.

Preferably, all of the solution of the diamine of the formula III and of the base are taken, the solution is warmed to the desired reaction temperature and the solution of the triazine component of the formula II is slowly metered in, with stirring. It is also possible however to take all the reaction components, and to heat the mixture to the desired reaction temperature. The degree of polycondensation n becomes in this case somewhat lower.

When the reaction has ended, the aqueous phase is separated off, the organic phase is dried—preferably by azeotropic distillation—and the solution is filtered. Filtration can be accelerated by addition of a filtration auxiliary, for example kieselguhr or fuller's earth. After the solvent has been evaporated off, the polyaminotriazine remains as a mass which is solid at room temperature and which can be comminuted as required.

The examples which follow illustrate the process in more detail, without restricting it to the procedure of the examples.

EXAMPLE 1

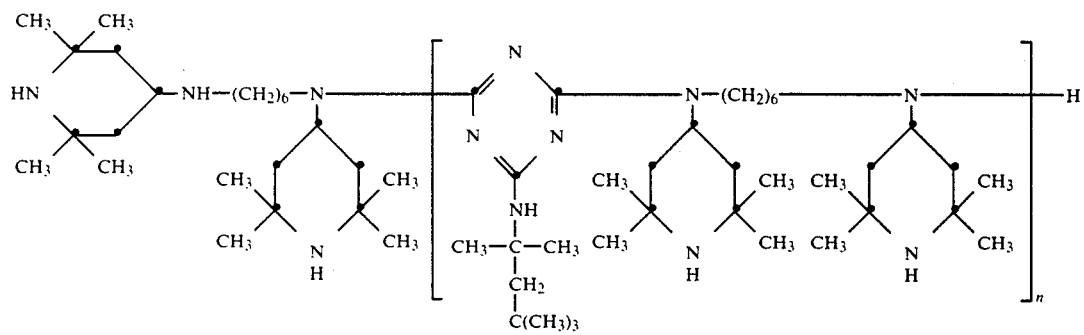

413.7 g (1.05 mols) of N,N'-bis-(2,2,6,6-tetramethyl-4-piperidyl)-hexamethylenediamine and 175 g of 50% aqueous sodium hydroxide solution are introduced into a 2.5 l low-pressure autoclave at 180° C. A solution of 276.5 g (1.0 mol) of tert.-octylamino-dichloro-s-triazine (prepared from cyanuric chloride and tert.-octylamine) in 450 g of xylene is metered into the mixture, with stirring, as follows: 85% of the xylene solution within 3 hours, and then the remaining 15% within 4 hours. A maximum pressure of 0.7 MPa is established. After the reaction mixture has been kept for another 5 hours at 185° C., it is cooled to 80°–90° C. and washed once with water. After the aqueous phase has been separated off, the xylene phase is dehydrated azeotropically and, after addition of the filtration auxiliary Celite 545, is filtered. The clear filtrate is evaporated at 200° C. in a rotary evaporator, the melt which remains is cooled and the resulting solid resin is comminuted.

Yield: 573.5 g = 93% of theory.

A mean molecular weight $\overline{M}_n$ (number-average) of 4,900 was found by gel permeation analysis and vapour pressure osmometry. This corresponds to a degree of polycondensation n of 7.5.

EXAMPLE 2

403.8 g (1.025 mols) of N,N'-bis-(2,2,6,6-tetramethyl-4-piperidyl)-hexamethylenediamine are reacted with the amounts of dichlorotriazine and sodium hydroxide solution given in Example 1 by a method similar to that described in Example 1. The same working up conditions give 583 g = 96% of theory. $\overline{M}_n = 6,300$, corresponding to n = 9.9.

EXAMPLE 3

The procedure described in Example 1 is repeated, except that 423.6 g (1.075 mols) of the diamine are used.

Yield: 5,914 g = 94.3% of theory. $\overline{M}_n = 3,660$, corresponding to n = 5.5.

What is claimed is:

1. An improved process for the preparation of a compound of formula I

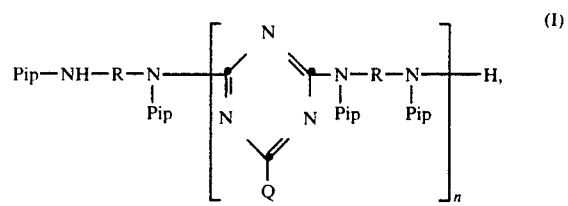

in which n is a number from 2 to 20, Pip is a radical of the formula

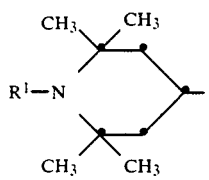

in which $R^1$ is hydrogen, $C_1-C_{12}$-alkyl, $C_3-C_8$-alkenyl, $C_7-C_{11}$-phenylalkyl, $C_2-C_8$-alkanoyl or $C_3-C_5$-alkenoyl, R is $C_2-C_{12}$-alkylene, which can be interrupted by —O— or —NR$^2$—, in which $R^2$ is hydrogen, $C_1-C_{12}$-alkyl, $C_3-C_{12}$-alkoxyalkyl, cycloalkyl, Pip or a divalent cycloaliphatic $C_6-C_{15}$-radical, and Q is a radical of the formula —OR$^3$, —NHR$^4$ or —NR$^4$R$^5$, in which $R^3$ is $C_1-C_{12}$alkyl, $C_3-C_{12}$-alkoxyalkyl, cyclohexyl, benzyl, phenyl, tolyl or Pip, $R^4$ is $C_1-C_{12}$-alkyl, $C_3-C_{12}$-alkoxyalkyl, $C_4-C_{12}$-dialkylaminoalkyl, allyl, benzyl, cyclohexyl, phenyl, tolyl or Pip and $R^5$ is $C_1-C_{12}$-alkyl, $C_3-C_{12}$-alkoxyalkyl or cyclohexyl, or $R^4$ and $R^5$ together with the N atom to which they are bonded form a 5- or 6-membered heterocyclic ring, by polycondensation of a dichlorotriazine of the formula II

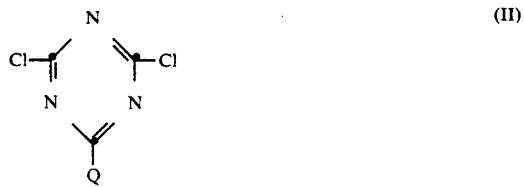

with a diamine of the formula III

in a molar ratio of 1 mol of dichlorotriazine of formula II to 1.0 to 1.2 moles of diamine of formula III in an inert organic solvent in the presence of a base wherein the improvement comprises carrying out the reaction in a water-immiscible organic solvent and an aqueous solution of an inorganic base at a temperature of 140°–220° C. under elevated pressure.

2. The process according to claim 1 for the preparation of a compound of the formula I in which $R^1$ is hydrogen or methyl, R is a straight-chain or branched $C_4$–$C_{12}$-alkylene radical and Q is a radical —$NHR^4$.

3. The process according to claim 2 for the preparation of compounds of the formula I in which R is hexamethylene and $R^4$ is a $C_6$–$C_{12}$-alkyl radical.

4. The process according to claim 1, wherein a concentrated aqueous solution of sodium hydroxide or potassium hydroxide is used as the base.

5. The process according to claim 1, wherein the diamine III is used in an excess of 1–10 mol %.

6. The process according to claim 1, wherein the reaction mixture is stirred so slowly that no turbulent mixing of the two phases occurs.

7. The process according to claim 1, wherein the reaction is carried out at 180°–190° C.

8. The process according to claim 1, wherein the triazine component of the formula II is slowly added, at the reaction temperature, to the solution of the diamine of the formula III.

* * * * *